United States Patent

Hammerle

[11] Patent Number: 5,332,961
[45] Date of Patent: Jul. 26, 1994

[54] RESISTIVE OIL QUALITY SENSOR

[75] Inventor: Robert H. Hammerle, Franklin, Mich.

[73] Assignee: Ford Motor Company, Dearborn, Mich.

[21] Appl. No.: 927,618

[22] Filed: Nov. 6, 1986

[51] Int. Cl.[5] .................................. G01R 27/02
[52] U.S. Cl. .................... 324/700; 338/195; 73/64.41
[58] Field of Search ............... 73/10, 54, 61 R, 64; 324/65 CR; 340/631, 634; 338/13, 14, 195, 229

[56] References Cited

U.S. PATENT DOCUMENTS

| | | | |
|---|---|---|---|
| 2,679,752 | 6/1954 | Metler | 436/6 |
| 3,060,721 | 10/1962 | Marsh et al. | 73/10 |
| 3,080,747 | 3/1963 | Kerst | 73/61.2 |
| 3,253,219 | 5/1966 | Littler | 324/71.1 |
| 3,821,642 | 6/1974 | Seymour | 324/65 CR |
| 3,857,094 | 12/1974 | Caldecourt | 324/65 CR |
| 3,936,737 | 2/1976 | Jefferies, Sr. | 324/65 CR |
| 3,951,161 | 4/1976 | Rohrback et al. | 324/65 CR |
| 4,019,133 | 4/1977 | Manley et al. | 324/65 CR |
| 4,135,100 | 1/1979 | Harada et al. | 250/573 |
| 4,142,402 | 3/1979 | Mattioli et al. | 73/61.2 |
| 4,217,544 | 8/1980 | Schmidt | 324/65 CR |
| 4,228,678 | 10/1980 | Slaton | 73/64.4 |
| 4,262,247 | 4/1981 | Olson et al. | 324/65 CR |
| 4,283,200 | 8/1981 | Bodmer et al. | 436/6 |
| 4,338,563 | 7/1982 | Rhoades et al. | 324/65 CR |
| 4,497,200 | 2/1985 | Tournier | 73/64 |
| 4,506,337 | 3/1985 | Yasuhara | 364/550 |
| 4,525,782 | 6/1985 | Wohlfarth et al. | 364/431.01 |
| 4,533,900 | 8/1985 | Muhlberger et al. | 340/52 R |

FOREIGN PATENT DOCUMENTS 207309 12/1982 Japan .................. 324/65 CR

OTHER PUBLICATIONS

Chrisfield et al. "Corrosion Monitoring in a Self-Maintenance System" IBM Technical Disclosure Bulletin vol. 20 No. 3 Aug. 1977 pp. 1124-1125.
"Encyclopedia of Electronics and Computers", S. P. Parker Editor,-McGraw-Hill Book Co., pp. 445-446.
Measuring Environmental Corrosivity, By R. C. Allen & M. J. Trzeciak, pp. 67-70 (IEEE Transactions on Components, Hybrids, and Manufacturing Technology, vol. CHMT 3, No. 1, Mar. 1980).
770642-Used Engine Oil Analyses, by P. A. Asseff, pp. 1-11 (undated).

Primary Examiner—A. D. Pellinen
Assistant Examiner—H. L. Williams
Attorney, Agent, or Firm—Paul K. Godwin, Jr.; Clifford L. Sadler

[57] ABSTRACT

An on-board oil quality sensor for use in an internal combustion engine formed of a pair of resisitve elements mounted on a common substrate, wherein one of the resistive elements is exposed to the oil for corrosion as the oil contaminants increase and the other resistive element is protectively sealed from the oil contaminants. Both resistive elements are exposed to the oil temperature and are suitable for monitoring by a bridge type circuit to determine the level of corrosive contaminants in the oil.

1 Claim, 1 Drawing

RESISTIVE OIL QUALITY SENSOR

BACKGROUND OF THE INVENTION

1. Field of the Invention

The present invention is directed to the field of systems for detecting the degradation of quality in oil used as a lubricant in internal combustion engines and more specifically to an on-board sensor used in such a system.

2. Description of the Prior Art

Conventionally, the manufacturers of internal combustion engines and vehicles which employ such engines have advised the purchasers of such products to remove and replace the lubricating oil at prescribed use intervals based upon hours or mileage accumulation. In addition, the manufacturers have also advised that more frequent replacement of the oil may be necessary when the engines are used under severe loading or environmental conditions.

In general, the oil used for lubricating an internal combustion engine should be changed before it loses its ability to prevent engine component wear. Three types of wear mechanisms have been identified as occurring when engine oil is degraded. The first wear mechanism is defined as corrosion caused by chemical attack. The second wear mechanism is erosion which is caused by metal-to-metal contact. The third wear mechanism is abrasion, caused by particles in the oil.

Corrosion does not occur if the oil contains sufficient additives, such as surface protecting compounds like zinc dithiophosphate and detergents, and antioxidants and alkalies to neutralize the corrosive contaminants formed by combustion. However, as the oil ages, these additives are depleted and contaminants such as hydroperoxides and acids, buildup in the oil. Corrosion begins when the peroxides and acids react with the metal surfaces.

Erosion does not occur if a sufficiently thick oil film remains between moving surfaces. The film thickness is controlled by its viscosity. If the oil is too viscous to be pumped throughout the engine, the film disappears where no oil is available. If the oil is too fluid, it is squeezed from between the bearing surfaces and metal-to-metal contact occurs. As fresh oil ages, its viscosity decreases at first due to the destruction of oil thickening additives; later the viscosity increases as oxidation causes polymerization. Erosion can occur if either mechanism causes the oil's viscosity to exceed safe limits. In addition, wear can occur when the antiwear compounds, such as zinc dithiophosphate, are depleted.

Abrasion is due to the accumulation of insoluble particles in the oil, such as airborne dust, carbon, degradation products from the oil and fuel, engine wear debris and corrosion products. Usually the oil suspends these particles and carries them to the oil filter. Fully-formulated oils contain detergents to help suspend these contaminants. However, when the oil loses its dispersive ability through aging, these particles are deposited throughout the engine, and rapid wear begins.

All three mechanisms appear to cause wear in modern engines, but it is usually very difficult to determine if one is responsible for more wear than the others. Indeed, many additives inhibit two wear mechanisms. When they are depleted, both wear mechanisms begin. For example, zinc dithiophosphate and its products adsorb on surfaces protecting them from corrosion and erosion. It also prevents corrosion by removing peroxides from the oil. Another example is detergents which protect surfaces from corrosion and suspend insoluble particles to reduce abrasion.

In general, two separate sensor techniques have been used to measure oil performance: analysis of engine wear and analysis of oil. Assuming that sensors to measure wear and oil are equally feasible to build, monitoring oil appears more desirable than monitoring wear. First, by monitoring engine wear one guarantees that wear of one or more components must begin be#ore the oil change indication is given. One would rather avoid wear, which, perhaps, could be done by making the sensor very sensitive, but this becomes increasingly difficult. Second, wear can occur in many different locations in the engine, such as at the cam shaft, followers, cam shaft bearings, rings, cylinders, main bearings,etc. Each would need a sensor, unless wear in all areas were correlated, which seems doubtful. On the other hand, the oil is well mixed so that measurement or analysis of oil properties in one location is sufficient.

Oil analysis techniques conventionally either determine the depletion of additives or the buildup of contaminants. Additives improve oil by enhancing important functions, such as antioxidation, viscosity, antiwear, anticorrosion and detergency, but in doing so they may undergo chemical reactions. Often intermediate reaction products still perform the original functions, but the final products do not. Unfortunately, laboratory analytical techniques are needed to measure the additives and their reaction products. Sensors that are sufficiently inexpensive and rugged enough for on-board use have not yet been developed, so that the analysis techniques can be used on a vehicle. Even, if such sensors were developed, each active compound must be analyzed, which may possibly require several sensors. Therefore, since it is considered impractical to provide a system that will determine oil quality onboard by analyzing the used oil additive concentration, one is forced confine measurements to the contamination of the oil.

Tests for the buildup of contaminants such as metals, insolubles, acidity and alkalinity have been established. Each test has been correlated to oil or engine performance. For example, insolubles are often correlated to engine cleanliness and wear, total acid numbers are also correlated to wear, and total base numbers to rust and varnish. Viscosity increase is often used as a indicator of oil oxidation. Silicon, which is aspirated into the engine as sand, is commonly correlated to wear.

The concentration of iron clearly results from wear of the iron parts of the engine. Much of the iron remains soluble in the oil as the salts of organic acids. Concentrations of 20 to 100 ppm iron are typical in oil used for 7,500 miles. Iron particles may be present in the oil when rapid wear is occurring, but they should be trapped by the associated oil filter. Copper concentration results from bearing wear when lead and copper bearings are used. Again, much of the copper remains soluble. Lead burned in the fuel can collect in the oil and thereby mask the lead-to-bearing wear correlation.

Results of contaminant tests generally show that large displacement engines cause a higher concentration of oil contamination than small displacement engines. This can be explained for oil oxidation degradation products in that they result from oxidation of the thin film of oil present on the cylinder wall. Large engines have more surface area in the cylinders than small engines so the rate of oxidation is higher. This affect is only somewhat offset by the fact that large engines also have more oil and rotate more slowly than small engines. Overall, the result may be a 20% slower decay of antioxidants in a 2.5 L engine compared to a 5.0 L engine.

Generally, on-board oil change indicators for automotive vehicles are based upon indirect measurements of engine oil condition by monitoring other parameters of the engine.

For instance, U.S. Pat. No. 4,533,900 describes a system which measures the distance traveled by the motor vehicle and, utilizing a preset service interval, modifies the interval to an earlier time based upon historical operating parameters such as engine speed, coolant temperature, oil temperature and/or fuel consumption rate on a weighted basis.

Similarly, U.S. Pat. No. 4,506,337 simulates engine oil wear by sensing the number of engine revolutions per time and the load on the engine. Those factors are used in calculating the amount of soot suspended in the lubricating oil.

U.S. Pat. No. 4,497,200 and 4,525,782 also describe similar systems for simulating or estimating oil degradation.

SUMMARY OF THE INVENTION

The present invention provides a unique sensor that directly measures oil performance and changes in the oil condition. The unique sensor employed measures oil corrosivity as a direct indication of oil condition and performance because corrosion of the sensor is a direct result of the aging of oil additives and the buildup of oil contaminants.

Therefore, it is an object of the present invention to provide a direct, low cost sensor that is suitable for on-board operation in an internal combustion engine to measure the condition of the engine lubrication oil.

It is another object of the present invention to provide a sensor and associated circuitry by which the measurement of oil corrosivity may be communicated to an associated signaling device to indicate when the oil should be changed.

The oil quality sensor used in the present invention includes a thermally conductive and electrically insulative substrate onto which a first electrically resistive copper element is mounted so as to have one of its copper surfaces exposed to the circulating engine oil. This sensor also includes a second electrically resistive element that is mounted on the substrate having a thermal coefficient of resistance that is substantially equal to that of the first resistive element. That second electrically resistive element is protectively sealed from the corrosive elements of the engine oil and functions as a standard comparative resistance.

DETAILED DESCRIPTION OF THE PREFERRED EMBODIMENT

Through experimentation, copper was determined to be the preferred material for use as a sensor to detect corrosion properties of oil. In addition, copper was found to be a material which barely corrodes in fully-formulated fresh oils but has measurable corrosion when the oil quality deteriorates. Therefore, even if an inferior oil is introduced into the crankcase of the engine that contains formulations which can corrode copper/lead bearings, the sensor employed in the present invention would appropriately be corroded and allow the associated circuit to provide an indication that the oil should be changed.

Figure 1:
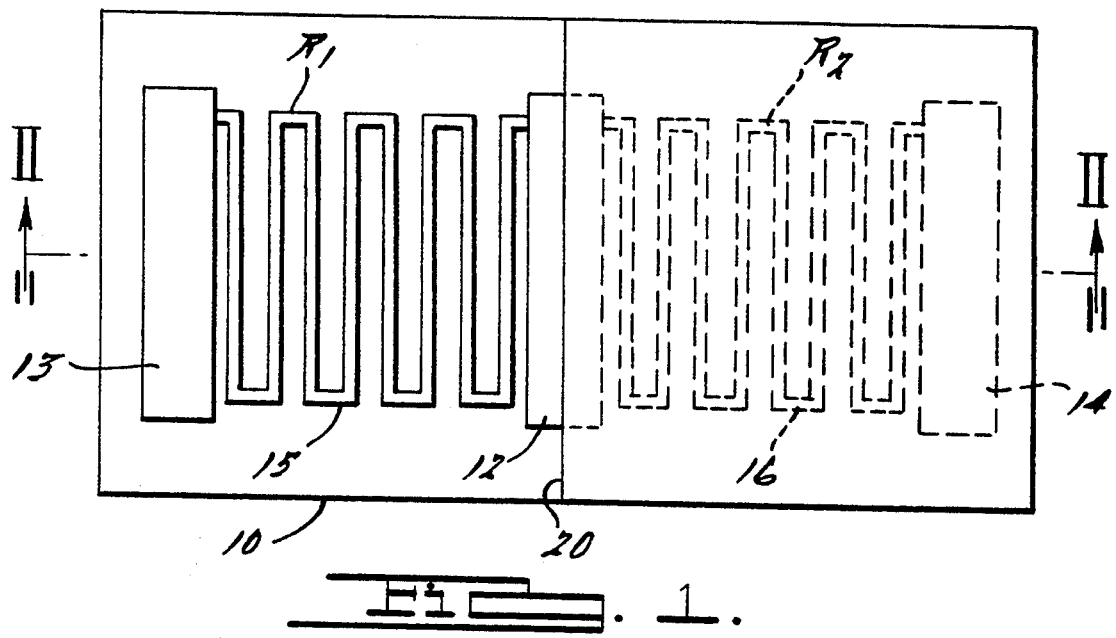
FIG. 1 is a plan view of the sensor employed in the present invention.

In FIG. 1, the sensor of the present invention is illustrated. A substrate 10, which would normally be formed from a thermally conductive but electrically insulative surfaced material such as silicon, provides support and thermal balance for the resistive sensors. In some installations it may be desired to increase the thermal conductivity between the resistive sensor elements by providing a substrate having a laminate structure with a copper or aluminum core sandwiched between electrically insulative layers.

Electrical terminal pads 12, 13 and 14 are shown distributed on one surface of the substrate 10 to provide interconnection to the resistive elements 15 and 16 which makeup the sensor. The first resistive element 15 ($R_1$) is shown deposited on the upper surface of the substrate 10 and electrically connected between terminal pads 12 and 13. The resistive element 15 is formed of copper and is exposed to the corrosive components of the oil when immersed in an associated oil pan of an engine (not shown). A second resistive element 16 ($R_2$) is indicated in phantom lines as being interconnected between terminal pads 12 and 14 and deposited on the upper surface of the substrate 10, adjacent the first resistive element 15. Resistive element 16 is protected from corrosion by the deposition of an inert coating 20. Both the exposed resistive element 15 and the protected element 16 have resistance values that are approximately equal and above 10 ohms in order to minimize power consumption of the sensor. The purpose of placing the two resistive elements 15 and 16 on the same substrate is, of course, to provide thermal compensation to the sensing circuit since both elements are immersed in the same liquid and are therefore at the same temperature. Accordingly, the thermal coefficient of resistance in each o#the resistive elements 15 and 16 must be substantially equal so the compensation will be achieved. Of course, the thermal coefficients of expansion for both the substrate 10 and the resistive elements 15 and 16 should be approximately equal so the the resistive values won't changed due to thermal stresses.

In the embodiment shown in FIG. 1, both resistive elements are formed of a thin metal copper foil glued to the substrate. However, other conventional methods of film deposition may be employed to deposit the copper resistive elements onto the substrate. The chemically inert layer 20 used to protect the resistive element 16 may be any suitable source such as polyimide, enamel, glass or ceramic. That material is selected to be suitable for the purpose of preventing corrosion of the resistive element 16. Each of the resistive elements 15 and 16 are, in the described embodiment, 10 ohms in value and made up of a copper ribbon having a 0.5 by 1.0 mil cross-section and a length of approximately 11 cm.

Figure 2:
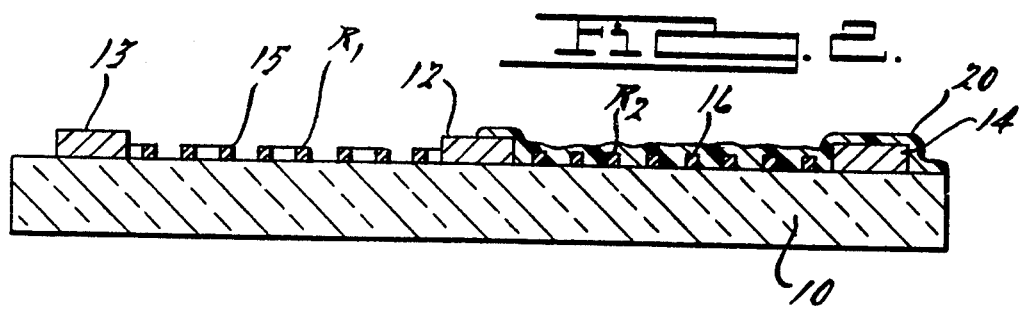
FIG. 2 is a cross-sectional view of the sensor taken along lines II—II in FIG. 1.
Figure 3:
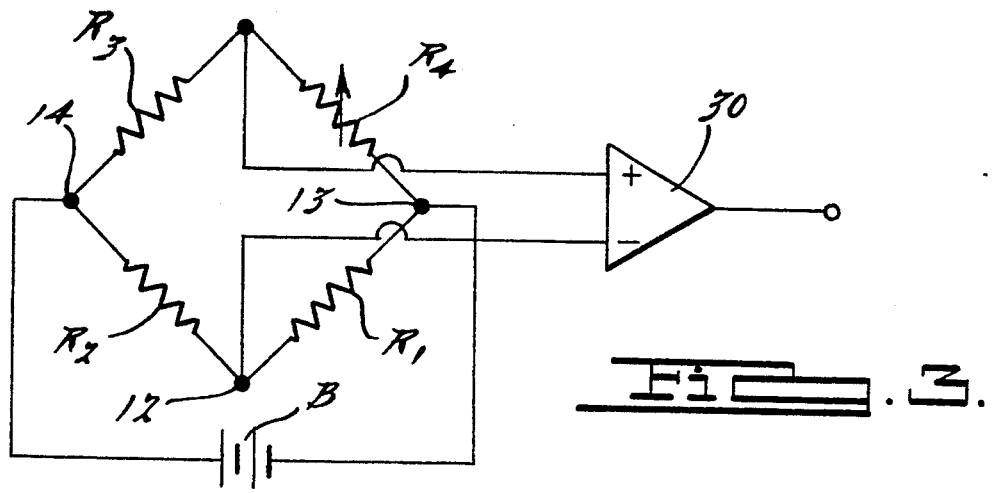
FIG. 3 is a schematic diagram of a circuit employed to be used with the sensor of the present invention.

The circuit employing the oil quality sensor of the present invention is shown in FIG. 3, wherein resistors $R_1$ and $R_2$ respectively corresponding to resistive elements 15 and 16 shown in FIGS. 1 and 2, are connected in separate legs of a Wheatstone Bridge circuit. Remotely located resistors $R_3$ and $R_4$ are electrically connected so as to form the other two legs of the bridge. Resistors $R_3$ and $R_4$ are substantially equal in value while resistor $R_4$ is adjustable in order to compensate for the eroded resistor $R_1$ in the event the bridge needs to be nulled after an oil change. An electrical DC power source "B" is connected between terminal pads 13 and 14. A differential amplifier 30 is connected between the terminal pad 12, at the junction of resistors $R_1$ and $R_2$, and the junction between resistors R3 and R4 to measure the offset voltage when the bridge becomes unbalanced due to corrosion of the resistor $R_1$. Corrosion of the resistor $R_1$, due to the increase in contaminants of the oil, causes the resistance value thereof to increase. The increase in $R_1$ resistance compared to that of $R_2$ and the other resistors in the bridge causes less current to flow in the leg of the bridge and an increase in the offset voltage. The signal output produced by the differential amplifier 30 can be employed in a conventional manner to provide a warning signal when the output thereof reaches a predetermined threshold corresponding to a sufficiently degraded oil quality.

It will be apparent that many modifications and variations may be implemented without departing from the scope of the novel concept of this invention. Therefore, it is intended by the appended claims to cover all such modifications and variations which fall within the true spirit and scope of the invention.

I claim:

1. A sensor for use in an internal combustion engine to measure the corrosive effects of lubricating oil, comprising:

a substrate having a thermally conductive and electrically insulative surface;

a first electrically resistive copper element mounted on said substrate surface, having a surface of said copper exposed;

a second electrically resistive element mounted on said substrate, having a thermal coefficient of resistance equal to that of said first resistive element; and a protective coating of a material that is impervious and inert with respect to the corrosive effects of said lubricating oil, deposited over a portion of said substrate and said second electrically resistive element to seal said second element and prevent its corrosion by said oil;

said first and second resistive elements being immersed in oil of said internal combustion engine so that said first resistive element is exposed to said oil and the resistance value of said first resistive element increases due to corrosion as said oil deteriorates from usage;

said sensor further includes a four leg Wheatstone bridge, in which said first and second resistive elements are electrically connected to define first and second legs, for comparing the resistance values of said first and second resistive elements and outputting an electrical signal corresponding to the difference in said values; and said Wheatstone bridge further includes third and fourth resistors electrically connected to define third and fourth legs of the bridge and physically remote from said first and second resistive elements, and one of said third and fourth resistors is adjustable so as to provide a balanced bridge when said oil is changed or said substrate, bearing said first and second resistive elements, is substituted with a new one.

* * * * *